United States Patent [19]

Taylor et al.

[11] Patent Number: 4,472,188

[45] Date of Patent: Sep. 18, 1984

[54] COMPOSITION PARTICULARLY FOR THE DEFOLIATION OF PLANTS

[75] Inventors: Kent Taylor, Tifton, Ga.; Reinhart Rusch, Berlin, Fed. Rep. of Germany

[73] Assignee: Schering Aktiengesellschaft, Berlin & Bergkamen, Fed. Rep. of Germany

[21] Appl. No.: 364,663

[22] Filed: Apr. 2, 1982

[30] Foreign Application Priority Data

Apr. 14, 1981 [DE] Fed. Rep. of Germany ....... 3116020
Apr. 14, 1981 [DE] Fed. Rep. of Germany ....... 3116013

[51] Int. Cl.$^3$ ............................................. A01N 57/00
[52] U.S. Cl. .......................................... 71/71; 71/73; 71/90
[58] Field of Search .................................. 71/71, 73, 90

[56] References Cited

U.S. PATENT DOCUMENTS

| | | | |
|---|---|---|---|
| 3,089,807 | 5/1963 | Trademan et al. ..................... | 71/71 |
| 4,261,726 | 4/1981 | Rusch et al. ............................ | 71/73 |
| 4,294,605 | 10/1981 | Arndt et al. ............................ | 71/73 |

OTHER PUBLICATIONS

Rusch et al., "1,2,3-thiadiazol-5-ylurea, etc.;" (1978), CA 89, No. 101907a, (1978).
Rusch et al., "Agent for Defoliating Plants," (1979), CA 91, No. 85277x, (1979).
Fabacher et al., "Apparent Potentiation of the, etc.;" (1976), CA 86, No. 151225d, (1977).
De Souza et al., "Effects of Propanil Herbicide, etc.; " (1980), CA 95, No. 75279x, (1981).
Samersov et al., "Insecticide-Herbicide Mixtures," (1974), CA 83, No. 23391f, (1975).
Macek, "Acute Toxicity of Pesticide, etc.;" (1975), CA 84, No. 100501s, (1976).

*Primary Examiner*—Glennon H. Hollrah
*Attorney, Agent, or Firm*—Michael J. Striker

[57] ABSTRACT

A composition for the defoliation of plants, particularly cotton plants, containing synergistic mixtures of 1-phenyl-3-(1,2,3-thiadiazol)-urea with O,O-dimethyl-O-(p-nitrophenyl)-thiophosphoric acid ester or O,O-diethyl-O-(p-nitrophenyl)-thiophosphoric acid ester in weight ratios from 1 part by weight 1-phenyl-3-(1,2,3-thiadiazol)-urea to 0.2 to 1000 parts by weight O,O-dimethyl-O-(p-nitrophenyl)-thiophosphoric acid ester or O,O-diethyl-O-(p-nitrophenyl)-thiophosphoric acid ester. With use of the composition the plants are not only advantageously defoliated, but also simultaneously freed of harmful insects.

4 Claims, No Drawings

COMPOSITION PARTICULARLY FOR THE DEFOLIATION OF PLANTS

BACKGROUND OF THE INVENTION

The invention concerns a composition particularly for the defoliation of plants, preferably cotton plants, containing mixtures of 1-phenyl-3-(1,2,3-thiadiazol-5-yl)-urea with O,O-dimethyl-O-(p-nitrophenyl)-thiophosphoric acid ester or O,O-diethyl-O-(p-nitrophenyl)-thiophosphoric acid ester.

1,2,3-thiadiazol-5-yl-ureas are already known as agents for the defoliation of plants (German Offenlegungsschrift DE-OS 25 06 690). These active agents, however, do not display a sufficient activity in all cases.

Moreover known are mixtures of 1,2,3-thiadiazol-5-yl-urea-derivatives with other defoliating agents, in which each of the indeed more or less strongly defoliating effective substances are mutually potentiated (activated) in their activity (German Offenlegungsschrift DE-OS No. 26 46 712). The synergistic activity of these mixtures is therefore dependent upon two already individually active compounds.

Agents of the known type display, though, only the described effect, without however being active against parasites of these plants, which must be controlled through additional use of appropriately active agents.

SUMMARY OF THE INVENTION

It is therefore an object of the present invention to provide a composition particularly for the defoliation of plants, with which the activity of the known active 1-phenyl-3-(1,2,3-thiadiazol-5-yl)-ureas is increased through the addition of a substance which is itself inactive, which simultaneously controls pests of these plants.

This object is attained according to the present invention by a composition, which is characterized by a content of 1-phenyl-3-(1,2,3-thiadiazol-5-yl)-urea of the formula

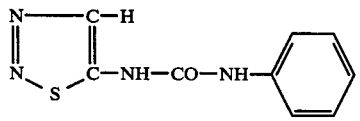

in mixture with
O,O-dimethyl-O-(p-nitrophenyl)-thiophosphoric acid ester of the formula

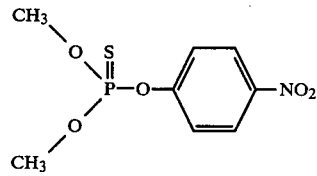

or
O,O-diethyl-O-(p-nitrophenyl)-thiophosphoric acid ester of the formula

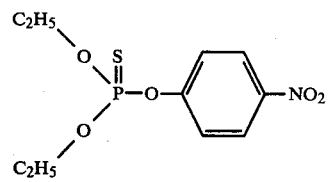

The composition according to the present invention displays in surprising manner an activity which is greater than that of the individual components. It is suitable therefore particularly for the defoliation of cotton plants, whereby in more ideal manner their insertion into gathering machines for the capsule harvest is made possible.

Also, other plants, for example citrus plants, can thereby be advantageously defoliated or influenced in their growth, such as for example demands for stoppage, lateral shoot formation, suppression of root growth with grasses and dicotyledons, such as hibiscus, apple and other coppices. It is understood that the composition according to the present invention can therefore be used advantageously not only for defoliation but also for growth regulation of plants.

It is known to the expert that defoliation is not an herbicidal activity, and that killing of the treated plants is undesirable, since the leaves remain connected to the killed plants and the productive portion of the plants is damaged. The sense of defoliation, i.e. to facilitate harvesting and to provide a cleaner harvest stock, is thereby lost. It is however necessary that the plants remain alive, while the leaves themselves are separated and fall off. This makes possible the further development of the productive portion of the plant, in the course of which leaf after-growths should be hindered. The composition according to the present invention achieves all of these objects in superior manner, so that with it the state of the art is enlarged.

In other respects, the composition according to the present invention attains the object of simultaneously controlling pests, in particular insects, so that with use of the composition the plants are not only advantageously defoliated, but also simultaneously can be freed of harmful insects.

The composition according to the present invention can also be used in mixture with other active agents, for example defoliating, plant protection, or pest control agents, according to the desired purpose.

A furtherance of activity and speed of action can generally be obtained, for example, through activity-increasing additives, such as organic solvents, wetting agents and oils. This permits a further decrease in the necessary amount of application for the real active agent.

The mixtures according to the present invention are appropriately used in the form of preparations, such as powders, spray agents, solutions, emulsions or suspensions, with the addition of liquid and/or solid carriers or diluting agents, and, if necessary, wetting, adhering, emulsifying and/or dispersing aids.

Suitable liquid carriers are, for example, water, aliphatic and aromatic hydrocarbons, such as benzene, toluene, xylene, cyclohexanone, isophorone, dimethylsulfoxide, dimethylformamide, and moreover mineral oil fractions.

As solid carriers, mineral earths, for example tonsil, silica gel, talc, porcelain clay, attaclay, limestone, silicic acid, and vegetable products, for example flour or meal, are suitable.

Appropriate surface active substances include: sodium or calcium lignin sulfonate, polyoxyethylene-alkylphenyl ether, naphthalenesulfonic acids and their salts, phenolsulfonic acids and their salts, formaldehyde condensate, fatty alcohol sulfate, salts of long-chain fatty acids, as well as substituted benzene sulfonic acids and their salts, by way of example.

The portion of the characterized mixture used in the different preparations can vary within wide limits. For example, the composition may contain about 5–95% by weight of the mixture, about 95–5% by weight liquid or solid carrier, as well as, if necessary, up to 50% by weight surface active substances, upon corresponding reduction of the amount of carrier.

The weight ratio of the components in the characterized mixture should amount to about 1 part by weight of 1-phenyl-3-(1,2,3-thiadiazol-5-yl)-urea to 0.2 up to 1000 parts by weight of O,O-dimethyl-O-(p-nitrophenyl)-thiophosphoric acid ester or O,O-diethyl-O-(p-nitrophenyl)-thiophosphoric acid ester, preferably 1 part by weight to 1 to 50 parts by weight, adjusted according to the sensitivity and capacity for resistance (hardiness) of the plants, the point in time of use, the climatic conditions and soil conditions.

The quantity to be used for the desired defoliation amounts as a rule to 1:10000 g mixture per hectare, preferably 10 to 1000 g mixture/ha.

Application of the composition follows in customary manner, for example with water as carrier in spray liquid quantities from about 100 to 1000 liter/ha. Use of the compositions according to the present invention in the so-called "low-volume" or "ultra-low-volume" technique is likewise possible.

1-phenyl-3-(1,2,3-thiadiazol-5-yl)-urea (common name: Thidiazuron), O,O-dimethyl-O-(p-nitrophenyl)-thiophosphoric acid (common name: Parathion-methyl) and O,O-diethyl-O-(p-nitrophenyl)-thiophosphoric acid (common name: Parathion) are known as such and can be produced according to known methods (see, for example, DE-OS No. 22 14 632 and DBP No. 814 152).

The novel features which are considered characteristic for the invention are set forth in particular in the appended claims. The invention itself, however, both as to its composition and its method of use, together with additional objects and advantages thereof, will be best understood from the following description of specific embodiments.

DESCRIPTION OF THE PREFERRED EMBODIMENTS

For production of the preparations, the following ingredients, by way of example, may be used:

| (a) | 95% by weight | Mixture |
| | 4% by weight | Kaolin (porcelain clay) |
| | 1% by weight | Surface-active substance based upon the sodium salt of N—Methyl-N—Oleyl-Taurine and the calcium salt of lignin sulfonic acid |
| (b) | 80% by weight | Mixture |
| | 10% by weight | Calcium salt of lignin sulfonic acid |
| | 3% by weight | Ammonium salt of monosulfuric acid-ester of tetraethyleneglycol-nonylphenylether |
| | 7% by weight | Colloidal silicic acid |
| (c) | 20% by weight | Mixture |
| | 70% by weight | Tonsil |
| | 8% by weight | Cell pitch |
| | 2% by weight | Wetting agent based upon a fatty acid condensation product |
| (d) | 5% by weight | Mixture |
| | 80% by weight | Tonsil |
| | 10% by weight | Cell pitch |
| | 5% by weight | Wetting agent based upon a fatty acid condensation product. |

The production of the preparations follows for example through mixing of the individual components in a canister and subsequent grinding down in a mill.

The following examples are based upon greenhouse tests, performed as a rule with cotton plants having 5 to 7 true foliage leaves, repeated four times. The compositions are used in the form of aqueous preparations based upon the above-given compositions.

Evaluation of the tests follows by counting of the leaves shed since application, and calculation of the portion in percent of the total number of leaves.

The following examples contain statements of active agents, their mixture, amount applied, as well as the determined percentage of defoliation. Values calculated according to the method of S. R. Colby, of the percent of defoliation expected to be obtained with the combination through the additive action under consideration, are partially given in parentheses (S. R. Colby, "Calculating Synergistic and Antagonistic Responses of Herbicide Combinations", Weeds, 15/1 (1967), pp. 20–22).

The calculations follow according to the formula:

$$E = X + Y - (XY)/100$$

in which
$X$ = percent defoliation with substance A at p kg active agent/ha
$Y$ = percent defoliation with substance B at q kg active agent/ha
$E$ = defoliation to be expected with A+B at p+q kg active agent/ha If the observed value is higher than the value E obtained according to Colby, then the combination has synergistic activity. The results of these Examples show clearly the activating effect upon the defoliation active substance 1-phenyl-3-(1,2,3-thiadiazol-5-yl)-urea through the itself inactive substance with insecticidal activity.

EXAMPLE 1

Young cotton plants are treated with the following given active agents. After one day, the percentage of shed leaves is determined. The results are given in the following table. The value for the combination shows the surprising increase in activity.

| Components | Amount Applied in g/ha | Defoliation in % | E (according to Colby) |
|---|---|---|---|
| 1-phenyl-3-(1,2,3-thiadiazol-5-yl)-urea (I) | 40 | 20 | |
| O,O—dimethyl-O—(p-nitrophenyl)-thiophosphoric acid ester (II) | 500 | 0 | |
| I + II | 40 + 400 | 95 | (20) |

EXAMPLE 2

Young cotton plants are treated and evaluated as in Example 1. The results are given in the following table:

| Components | Amount Applied in g/ha | Defoliation in % | E (according to Colby) |
|---|---|---|---|
| 1-phenyl-3-(1,2,3-thiadiazol-5-yl)-urea (I) | 20 | 33 | |
| | 80 | 48 | |
| O,O—dimethyl-O—(p-nitrophenyl)-thiophosphoric acid ester (II) | 600 | 0 | |
| I + II | 20 + 500 | 100 | (33) |

EXAMPLE 3

Young cotton plants are treated and evaluated as in Example 1. The results are given in the following table:

| Components | Amount Applied in g/ha | Defoliation in % | E (according to Colby) |
|---|---|---|---|
| 1-phenyl-3-(1,2,3-thiadiazol-5-yl)-urea (I) | 40 | 20 | |
| O,O—dimethyl-O—(p-nitrophenyl)-thiophosphoric acid ester (II) | 1100 | 0 | |
| I + II | 40 + 40 | 48 | |
| | 40 + 80 | 52 | |
| | 40 + 200 | 86 | |
| | 40 + 400 | 95 | |
| | 40 + 1000 | 95 | |

EXAMPLE 4

Young cotton plants are treated and evaluated as in Example 1. A portion of the plants are exposed to a sprinkling, corresponding to 10 l water per m², four hours after application of the active agents. The results are given in the following table. They make clear the very low rain sensitivity of the combination.

| Components | Amount Applied in g/ha | Defoliation in % Without Sprinkling | Defoliation in % With Sprinkling |
|---|---|---|---|
| 1-phenyl-3-(1,2,3-thiadiazol-5-yl)-urea (I) | 100 | 50 | 15 |
| O,O—dimethyl-O—(p-nitrophenyl)-thiophosphoric acid ester (II) | 600 | 0 | 0 |
| I + II | 100 + 500 | 90 | 85 |

EXAMPLE 5

Young citrus plants with 12 to 15 foliage leaves are sprayed with the following active agents. A portion of the plants is exposed to a sprinkling corresponding to 10 l water per m² (=10 mm rain). The results in the table show very clearly the decreased sensitivity to rain resulting through use of the combination of components.

| Components | Amount Applied in g/ha | Defoliation in % Without Sprinkling | Defoliation in % With Sprinkling |
|---|---|---|---|
| 1-phenyl-3-(1,2,3-thiadiazol-5-yl)-urea (I) | 300 | 29.6 | 7 |
| O,O—dimethyl-O—(p-nitrophenyl)-thiophosphoric acid ester (II) | 800 | 0 | 0 |
| I + II | 300 + 800 | 52.6 | 46 |

EXAMPLE 6

Young cotton plants are treated with the following active agents. After 1 day, the percentage of shed leaves is determined. The results are given in the following table. The value for the combination shows the surprising increase in activity.

| Components | Amount Applied in g/ha | Defoliation in % | E (according to Colby) |
|---|---|---|---|
| 1-phenyl-3-(1,2,3-thiadiazol-5-yl)-urea (I) | 20 | 33 | |
| | 80 | 48 | |
| O,O—diethyl-O—(p-nitrophenyl)-thiophosphoric acid ester (II) | 600 | 0 | |
| I + II | 20 + 500 | 62 | (33) |

EXAMPLE 7

Young cotton plants are treated and evaluated as in Example 6. The results are given in the following table:

| Components | Amount Applied in g/ha | Defoliation in % | E (according to Colby) |
|---|---|---|---|
| 1-phenyl-3-(1,2,3-thiadiazol-5-yl)-urea (I) | 20 | 27.8 | |
| | 40 | 38.9 | |
| O,O—diethyl-O—(p-nitrophenyl)-thiophosphoric acid ester (II) | 1100 | 0 | |
| I + II | 20 + 1000 | 72.2 | (27.8) |
| | 40 + 1000 | 88.9 | (38.9) |

It will be understood that each of the elements described above, or two or more together, may also find a useful application in other types of compositions different from the types described above.

While the invention has been illustrated and described as embodied in a composition particularly for the defoliation of plants, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Composition particularly for the defoliation of plants, consisting essentially of an effective amount and ratio of 1-phenyl-3-(1,2,3-thiadiazol-5-yl)-urea in mixture with O,O-dimethyl-O-(p-nitrophenyl)-thiophosphoric acid ester or O,O-diethyl-O-(p-nitrophenyl)-thiophosphoric acid ester.

2. Composition according to claim 1, containing individual components in a weight ratio of 1 part by weight 1-phenyl-3-(1,2,3-thiadiazol-5-yl)-urea to 0.2 to 1000 parts by weight O,O-dimethyl-O-(p-nitrophenyl)-thiophosphoric acid ester or O,O-diethyl-O-(p-nitrophenyl)-thiophosphoric acid ester.

3. Composition according to claim 2, wherein said weight ratio is 1 to 1–50.

4. Composition according to claim 1, in mixture with inert carrier and/or adjuvants.

* * * * *